United States Patent [19]

Dianis

[11] Patent Number: 4,668,837

[45] Date of Patent: * May 26, 1987

[54] PHOSPHORUS MODIFIED MAGNESIUM SILICATE

[75] Inventor: William P. Dianis, Midland, Mich.

[73] Assignee: The Dow Chemical Company, Midland, Mich.

[*] Notice: The portion of the term of this patent subsequent to May 22, 2001 has been disclaimed.

[21] Appl. No.: 554,038

[22] Filed: Nov. 21, 1983

[51] Int. Cl.$^4$ .............................................. C07C 2/68
[52] U.S. Cl. .................................... 585/466; 585/467
[58] Field of Search ................................. 585/466, 467

[56] References Cited

U.S. PATENT DOCUMENTS

| | | | |
|---|---|---|---|
| 3,893,910 | 7/1975 | Robson | 208/135 |
| 4,002,698 | 1/1977 | Keeding | 585/466 |
| 4,356,338 | 10/1982 | Young | 585/466 |
| 4,423,266 | 12/1983 | Young | 585/466 |
| 4,499,320 | 2/1985 | Garces | 585/467 |

*Primary Examiner*—Curtis R. Davis

[57] ABSTRACT

Porous crystalline magnesium silicates modified by addition of phosphorus in an amount from about 0.25 percent to about 30 percent by weight.

4 Claims, No Drawings

PHOSPHORUS MODIFIED MAGNESIUM SILICATE

BACKGROUND OF THE INVENTION

The present invention relates to novel phosphorus modified, porous magnesium silicates. More particularly the present invention relates to such phosphorus modified porous magnesium silicates having catalytic properties that are usefully employed in the alkylation of aromatic compounds.

Porous aluminosilicates, i.e., zeolites, especially highly siliceous forms thereof, such as ZSM-5, silicalite, ZSM-35, etc., are well-known in the art. Typically such compounds are porous crystalline frameworks based on an extended three-dimensional network of $SiO_4$ and greater or lesser amounts of $AlO_4$ tetrahedra linked to each other by shared oxygens. In U.S. Pat. No. 4,049,573 (Kaeding) it was disclosed that zeolites such as ZSM-5, ZSM-11, ZSM-12, ZSM-35, ZSM-38, etc., could be beneficially treated by impregnation with modifying substances including phosphorus compounds thereby preparing zeolitic catalysts having deposited or occluded modifying species. These modifiers are believed to affect the acid sites of the zeolites and were found to be useful catalysts in hydrocarbon conversion processes.

In U.S. Pat. No. 4,002,698, phosphorus modified aluminosilicates that are particularly suited for the alkylation of toluene were described. Preferred compounds possessed a silica/alumina ratio of at least about 12 and were modified by the addition thereto of at least 0.5 percent by weight phosphorus.

Numerous additional references teach that aluminosilicate zeolites may optionally further contain modifying substances including phosphorus. The phosphorus may be added by contacting the zeolite with an organic phosphorus compound or an inorganic phosphorus compound such as quaternary ammonium phosphate salts. Illustrative of such references are U.S. Pat. Nos. 4,140,726; 4,276,437; 4,276,438; 4,275,256; 4,278,827; 4,259,537; 4,230,894; 4,250,345; 3,962,364; 4,270,017, etc.

In 1972, U.S. Pat. No. 3,702,886 (Argauer) issued for a synthetic zeolite termed ZSM-5 and method for making same. This patent disclosed a zeolite having a $SiO_2/Al_2O_3$ molar ratio from about 5 to 100. The main claim characterized ZSM-5 by reference to a table of X-ray diffraction lines (see Table I infra) and the following composition in terms of mole ratios of oxides $$0.9 \pm 0.2\ M_{2/n}O:Al_2O_3:YSiO_2:ZH_2O$$

wherein M is at least one cation having a valance n, Y, is at least 5 and Z is between 0 and 40.

TABLE I

| ZSM-5, Interplanar Spacing d(A) | | | |
|---|---|---|---|
| 11.1 ± 0.2 | 6.30 ± 0.1 | 5.01 ± 0.1 | 3.71 ± 0.05 |
| 10.0 ± 0.2 | 6.04 ± 0.1 | 4.60 ± 0.08 | 3.04 ± 0.03 |
| 7.4 ± 0.15 | 5.97 ± 0.1 | 4.25 ± 0.08 | 2.99 ± 0.02 |
| 7.1 ± 0.15 | 5.56 ± 0.1 | 3.85 ± 0.07 | 2.94 ± 0.02 |

According to Mobil scientists, the ZSM-5 aluminosilicate is prepared by including nitrogenous organic molecules such as tetrapropyl ammonium bromide in the reaction mixtures. For very high $SiO_2/Al_2O_3$ preparations, no aluminum need be deliberately added since it is present as an impurity in the reactants. The organic molecules are incorporated into the framework structure as it forms and these as-synthesized materials are termed "nitrogenous zeolites". Application of high temperatures will free high $SiO_2/Al_2O_3$ materials of these organic components without altering the basic framework structure, D. M. Olson et al., "Chemical and Physical Properties of the ZSM-5 Substitutional Series", *J. Catal.*, 61, 390–396 at 391 (1980).

SUMMARY OF THE INVENTION

According to the present invention, there are provided novel porous, crystalline magnesium silicates modified by the addition thereto of phosphorus in the amount from about 0.25 percent by weight to about 30 percent by weight.

The porous crystalline magnesium silicate may be further described as follows. The amount of magnesium present in this silicate may vary. However, for all compositions of the present invention, it is essential that some magnesium which is not ion-exchangeable by conventional techniques be present in the silicate. Conventional techniques of ion-exchange are presented in Breck, *Zeolite Molecular Sieves*, John Wiley & Sons (1974). Other elements may be present in porous magnesium silicates as impurities such as aluminum, germanium, gallium, etc., or chemicals may be deliberately added either to modify or improve the properties of the magnesium silicate or for other advantageous reasons, for example, to ameliorate process parameters. Suitable additional chemicals include primarily chromium, iron, copper, barium and boron.

These porous magnesium silicates have a composition which may be expressed according to the following formula in terms of the molar ratios of oxides on a dry basis:

$$(M_{2/n}O)_p(MgO)_x(R_2O_3)_y(SiO_2)_z$$

wherein M is at least one ion-exchangeable cation having a valence of n; R is at least one element (with valence 3+) which is not ion-exchangeable by conventional means; $x/z > 0$; $y/z > 0$; $p/n > y$; and p, x, z are positive numbers and y is a positive number or zero. By dry basis is meant material which has been heated in air at about 500° C. for a period of one hour or more. The invention is not limited to use only of such dried material or said oxide forms, rather the composition of the porous magnesium silicates employed herein may be presented in terms of oxides and on a dry basis (as in the above formula) in order to provide a means for identifying such compositions.

The porous magnesium silicates modified by addition of phosphorus according to the present invention are prepared by hydrothermal methods from a variety of silicate and magnesium sources leading to products, all of which incorporate magnesium into the structure of the resulting porous crystalline magnesium silicate.

Incorporation of phosphorus may be performed by any suitable technique. Advantageously, the previously prepared porous magnesium silicate is physically contacted with a suitable phosphorus compound optionally in a solvent. Removal of the solvent as, for example, by evaporation, results in isolation of the phosphorus modified porous magnesium silicate. Once prepared, the phosphorus modified porous crystalline magnesium silicates may be handled like previously known alkylation catalysts. The composition may be mixed with binders such as clays and compressed into pellets, pulverized or otherwise machined prior to use and calcined. The phosphorus modified porous crystalline magnesium silicates of the invention are useful catalysts in the alkylation of aromatic compounds such as benzene, toluene, etc., with a variety of alkylating agents including olefins, primary alcohols, etc.

DETAILED DESCRIPTION OF THE INVENTION

The term crystalline when used in this document refers to materials which are recognized by those skilled in the art as having a highly ordered structure. Three dimensional periodicity is characteristic of a highly ordered structure. The skilled artisan recognizes that evidence of such periodicity may be presented by catalytic reactivity, infrared spectroscopy or other means of analysis as well as by the commonplace X-ray diffraction analysis. Porous magnesium silicates employed in the present invention are "crystalline" as that term is characterized above even if said silicates appear amorphous to X-ray diffraction analysis if a skilled artisan recognizes a highly ordered structure by other evidence. A recent article by P. A. Jacobs et al., "Evidence of X-ray Amorphous Zeolites", *J.C.S. Chem. Comm.*, 591, 1981, is hereby incorporated by reference in its entirety in this document.

By the term "porous" are meant those silicates having a framework structure containing cavities capable of allowing the entrance or absorbance of molecules such as water, nitrogen or toluene, etc.

Due to the differences in ionic radii of $Si^{IV}$ (0.41 Å) and $Al^{III}$ (0.50 Å) replacement of Si by Al in $TO_4$ sites will cause a unit cell volume expansion in most zeolites. The degree of unit cell volume expansion will depend on the amount of Al substitution for Si in the $TO_4$ sites. If the substitution is low, as in some ZSM-5 and silicalite zeolites, high resolution, calibrated X-ray diffraction techniques must be utilized to detect the expansion.

Similarly, in the present invention, it is believed that nonion-exchangeable Mg is contained in the magnesium silicate lattice. Replacement of $Si^{IV}$ (0.41 Å) by $Mg^{II}$ (0.65 Å) in $TO_4$ sites will also cause a unit cell expansion. Once again, the amount of Mg substitution for Si, will influence the degree of cell volume expansion.

Evidencing element location in a framework lattice structure by determining cell volume expansion (contraction) has been done by others skilled in making silicates. See, e.g., M. Taramasso, G. Perego and B. Notari, "Molecular Sieve Borosilicates", *Proceedings of the Fifth International Conference on Zeolites*, 40–48 at 44 (Heyden & Sons Ltd.) (1980).

High resolution X-ray powder diffraction data were obtained from Huber-Guinier powder diffraction cameras equipped with Ge and quartz monochromators for providing $CuK_{\alpha 1}$ and $FeK_{\alpha 1}$ radiation, respectively. The films were calibrated, with well-known internal standards such as NBS Si (NBS Circular 539 Vol. 9, p. 3) or $As_2O_3$, scanned with a densitometer and the resulting data profile fit by techniques described in: J. W. Edmonds and W. W. Henslee, *Adv. in X-ray Anal.*, 22, 143 (1978) and J. W. Edmonds, "Precision Guinier X-ray Powder Diffraction Data", NBS Special Publication 567, *Proceedings of Symposium on Accuracy in Powder Diffraction Held at NBS, Gaithersburg, MD*, June 11–15, 1979 (Issued Feb. 1980) (the papers are hereby incorporated by reference). The calibrated data were least-squares refined and fitted to obtain accurate cell dimensions and volumes.

Using data from the method described above and using single crystal X-ray crystallographic data from the literature, the cell volume for porous magnesium silicates employed in the present invention where $Mg^{II}$ is believed to replace $Si^{IV}$, can be compared to the cell volume of silicalite which has $Si^{IV}$ in all the $TO_4$ sites. Typical data are shown in Table II, for either anhydrous zeolites or calcined zeolites. (Minimum calcination of 500° C. for 1 hour).

TABLE II

| Compound | Cell Volumes Volume (A³) | Reference |
|---|---|---|
| Silicalite | 5306 | 1 |
| Silicalite | 5305 | 2 |
| Magnesium Silicate | 5347 | 2 |
| Magnesium Silicate | 5349 | 2 |

[1] Cell volumes were obtained from the lattice parameters given in an article by E. M. Flanigen, J. M. Bennett, R. W. Grose, J. P. Cohen, R. L. Patton, R. M. Kirchner and J. V. Smith, Nature, 271, 512 (1978).
[2] Cell volumes were calculated using the National Bureau of Standards - Geological Survey Lattice Parameter Refinement Program written by Dan Appleman (available through NTIS) on XRD data obtained on samples made either according to the process explained herein or according to the silicalite patent.

The above values are typical examples of cell volumes of porous magnesium silicates employed in the invention and a highly siliceous zeolite such as silicalite. The difference between these volumes shows a cell volume expansion. The exact amount of expansion will be composition dependent. The porous magnesium silicate compounds employed in the present invention will exhibit unit cell volume expansion when compared to silicalite, but expansion is not limited to that derived from the data shown in Table II. It is believed that the above-mentioned unit cell expansion evidences the placement of magnesium as a part of the lattice framework structure. It is believed, without wishing to be bound by that belief, that altering the $SiO_2/MgO$ ratio varies the pore size and volume, framework density and refractive index of the resulting magnesium silicates. If small ranges of the $SiO_2/MgO$ ratios are utilized, the ability to detect volume, pore size and density differences will be dependent on the resolution capabilities of the analytical technique used.

Samples of compositions of the present invention whose crystallite size is appropriate to produce a distinct X-ray powder diffraction trace, have a pattern which includes at least the interplanar d spacings listed in Table III.

TABLE III

| Magnesium silicate, interplanar spacings d(A) |
|---|
| 11.2 ± 0.2 |
| 10.1 ± 0.2 |
| 10.0 ± 0.2 |
| 9.8 ± 0.2 |
| 6.0 ± 0.2 |
| 5.8 ± 0.2 |
| 5.6 ± 0.2 |
| 4.26 ± 0.1 |
| 3.85 ± 0.05 |
| 3.81 ± 0.05 |
| 3.74 ± 0.03 |
| 3.72 ± 0.03 |
| 3.64 ± 0.03 |

The range cited is due to unit cell volume expansion with decreasing $SiO_2/MgO$ ratio. Magnesium silicates with low Mg content in the $TO_4$ sites will be near the low d spacing limit and those with high Mg content in TO$_4$ sites will be near the high d spacing limit.

The magnesium silicates employed in the present invention are further characterized by a minimum of two reflections at 10.1±0.3 Å and a minimum of four reflections between 3.72 and 3.90 Å.

These values were obtained by Huber-Guinier techniques (preferred method) mentioned previously or by a Philips Electronics X-ray powder diffraction unit equipped with: scintillation-counter detector, graphite monochromator, and a strip chart recorder. The recorded reflections were identified by their two theta locations, after these locations were calibrated with an internal standard. The standard used was either NBS Si (NBS Circular 539, Vol. 9, p. 3) or As$_2$O$_3$. The magnesium silicate diffraction peaks at approximately 10.0 and 3.81 Å can often be obscured in poorly crystalline samples or in low-resolution X-ray diffraction data.

X-ray analyses of magnesium silicates employed in the present invention reveal distinct differences in the diffraction patterns as a result of specific treatments given to these magnesium silicates. Intensity changes are observed and lines may appear, disappear or merge depending on the exact calcination procedure utilized. Ion-exchange of these silicates may also cause changes in certain cases. Several authors have made similar observations on related materials like zeolite ZSM-5. See H. Nakamoto and H. Tarahashi, *Chem. Lett.*, 1013-1016 (1981). Regardless of the causes of the above-mentioned changes, they are expected by those people skilled in the art of analyzing porous crystalline silicates.

The magnesium silicates employed in this invention are characterized also by infrared analysis. The use of infrared analysis is recognized as a standard method in the characterization of inorganic and organic materials and has been used in the study of both natural and synthetic zeolites. See for example, E. M. Flanigen et al., *Adv. Chem. Series*, Vol. 101, p. 201-229, 1971. See also P. A. Jacobs, supra. For examples from the patent literature pertaining to the use of infrared analysis in zeolite characterization, see U.S. Pat. No. 4,257,885 to R. W. Grose and E. M. Flanigen and references included therein.

Porous magnesium silicates employed in the present invention exhibit unique features in the 1300-400 cm$^{-1}$ region. Many compositions employed in this invention exhibit at least two distinct bands in the 1200-980 cm$^{-1}$ region. Preferred compositions employed in the present invention exhibit these two distinct bands and also characteristic infrared bands at 1225±10 cm$^{-1}$, 800±20 cm$^{-1}$, Q620±10 cm$^{-1}$, 550±20 cm$^{-1}$ and 450±20 cm$^{-1}$.

Without wishing to be bound by any theory, it should be recognized that bands located between 1200-980 cm$^{-1}$ may be due to asymmetric stretch of TO$_4$ units in zeolites and silicates, see, e.g., Flanigen et al., "Molecular Sieve Zeolites-1," *Adv. Chem. Series*, 101, 201 A.C.S. (1971). It is believed without being bound by that belief that the band found nearest to 980 cm$^{-1}$ in the magnesium silicates employed in the present invention is due to silanol groups of the form —Si(OH)$_3$, >Si(OH)$_2$, →SiOH, or to their corresponding silicate forms.

Differential thermal analysis (DTA) is one of the thermal methods used in the literature as an aid in zeolite characterization. See D. W. Breck, *Zeolites Molecular Sieves*, John Wiley, 1974. See also European Patent Office Document No. 14,545 (Chu et al.), Jan. 24, 1980.

Compositions employed in the present invention may be analyzed by DTA methods. When using a Dupont ® 990 thermal analysis unit equipped with a 1200° C. furnace, a 10-mg sample is tested against alumina as a reference material (both contained in platinum crucibles). The heating rate for the system is 20° C. per minute in air with an air flow rate of 50 cc per minute. Under these conditions, one observes a distinct exotherm at 870°±30° C. X-ray diffraction (XRD) analysis of the sample both before and after the exotherm yields at least the interplanar d spacings listed in Table III, supra.

The magnesium silicate materials employed in this invention have ion-exchange properties. The ion-exchange capacity of traditional zeolites is associated with their aluminum content. The ion-exchange properties of the magnesium silicates employed in this invention are not necessarily dependent upon any one of its particular components. Indeed it is believed, without wishing to be bound to this belief, that the ion-exchange capacity of the present invention is due to a combination of factors. Among them are: the magnesium content, the trivalent metal ion content and also to the presence of internal silanol moieties within the silicate framework which under appropriate conditions can participate in the ion-exchange process.

Even though a relationship among the composition and the ion-exchange capacity of these solids is recognized, the magnesium silicates employed in the present invention is not restricted by the traditional "linear relationship" between composition and ion-exchange capacity, characteristic of traditional zeolites.

The exchangeable cations in zeolite compositions often play a critical role in their synthesis by hydrothermal methods. In certain cases, a particular cation is required to obtain a given zeolite, for example, sodium is said to be required to produce zeolite X from aluminosilicate gels. Apparently the cation plays a template role in the formation of certain structures and/or acts as a crystallization promoter. The magnesium silicates employed in this invention do not appear to require a particular alkali metal cation for their formation. Magnesium silicates employed in the present invention may be obtained from magnesium silicate gels in the presence of several alkaline metal salts including sodium or potassium salts. The presence of sodium or potassium ions during and/or after the synthesis may affect certain properties of the final product in applications which are susceptible to drastic changes by subtle differences such as catalysis and adsorption. Salts other than sodium and potassium may have similar effects.

In the synthesis of traditional zeolites the source of silica may be a critical factor in the preparation of certain zeolites. In the case of the present invention, the source of silica appears to have an effect in the morphology of the crystalline product. There are many examples in the literature relating morphology to a variety of useful properties of porous crystalline silicates like catalytic applications, ion-exchange, adsorption, etc.

Typically, the porous magnesium silicates employed in the present invention are made by hydrothermal methods using one of many sources of silicon such as one of the commercially available soluble silicates or water glass solutions, amorphous silica, colloidal silica, silica gels, fumed silica or an organosilicate like (EtO)$_4$Si. Advantageously employed are two commercially available sources: a colloidal silica sold by the du Pont de Nemours Company under the trademark Ludox SM ® and a sodium silicate sold by the Philadelphia Quartz Company under the trademark Philadelphia Quartz Sodium Silicate N ®.

The source of magnesium usually is one of its water-soluble salts, magnesium chloride, acetate, sulfate, nitrate, etc., or a complex ion like $Mg(NH_3)_6^{2+}$, $Mg(EDTA)^{2-}$, etc., or a slightly soluble compound like $Mg(OH)_2$, $MgF_2$, etc. A magnesium chloride salt is a preferred source of magnesium.

Besides these components the reaction mixture will contain a solvent such as water, along with alkali metal ion salts such as, chlorides, sulfates or hydroxides of sodium, potassium, rubidium or cesium. The solvent may be added separately to the reaction mixture or may already be present with one of the reactants such as the silica source. Water is the preferred solvent.

A material which is believed, without wishing to be bound by that belief, to act as a crystallization promoter and is hereinafter termed a "crystallization promoter" is utilized in the process of making the porous crystalline magnesium silicates employed in the present invention. Typically, this crystallization promoter is (or is formed from) an organic nitrogen compound such as quaternary ammonium ion salts, or hexamethylene diamine, but may also be other compounds such as seed crystals typically of compositions similar to those crystals sought from the process. In particular, tetrapropyl ammonium ion salts are often used with tetrapropyl ammonium bromide and tetrapropyl ammonium hydroxide being preferred.

In a typical method of making these magnesium silicates, a magnesium source, a crystallization promoter, an alkali metal ion salt and a solvent are combined. The pH of this combination of chemicals is usually adjusted and the combination is further combined with a mixture of a silica source and a solvent to give a reaction mixture typically having a pH of about 11. The pH may advantageously be adjusted either above or below a pH of 11 to modify certain crystallization or process parameters such as the solubility of magnesium in the mixture, formation of precipitates, rates of crystallization, etc. The pH is adjusted as desired using acids or bases such as $H_2SO_4$ or NaOH and may be adjusted before, after and/or during the mixing step of the reactants.

The reaction mixture is vigorously mixed at room temperature for a sufficient time to produce an apparently homogeneous gel. Typically the rate of mixing is sufficiently vigorous to produce a satisfactory slurry or gel within one minute.

The mixture resulting from the above procedure is allowed to crystallize into compositions employed in the present invention. Preferably, crystallization takes place at temperatures above room temperature to increase the rate of crystal growth. Usually about 150° C. is used with autogeneous pressure. Higher or lower temperatures may be advantageously employed depending upon the process or product parameters desired, e.g., larger crystals are generally formed with lower temperatures and the rate of crystallization increases with higher temperatures. When quaternary ammonium ion salts are used as crystallization promoters, temperatures above 200° C. are avoided to prevent their decomposition.

Suitable time periods for the crystallization may be determined by analysis of reaction mixture samples at intervals. The crystallization time will vary depending upon the reactants or the particular process parameters chosen. Crystallization times of one to five days are not uncommon.

During the crystallization step, stirring may be advantageously employed to facilitate product formation. The rate and type of stirring may affect crystallization parameters such as the rate of crystallization, uniformity of the product and crystal size. The effect of this parameter and optimum adjustment is dependent upon other parameters and is believed to be within the skill of the art to determine without undue experimentation.

Following crystallization it is often desirable to filter the crystallized mixture using a water wash to remove the mother liquor and then to heat the crystals to about 110° C. to remove water and thereby produce a convenient free-flowing powder.

The compositions as made by the above procedure may contain organic moieties which, if desired, may be removed by known methods such as calcination in an oxygen-containing atmosphere at a temperature sufficient to decompose the organic moieties. Calcination at about 500° C.-W-600° C. for approximately an hour is sufficient to remove commonly present organic moieties.

The magnesium silicates employed in the invention may be beneficially modified by techniques well-known in the art which treat said silicates with acids, salts or other ions or molecules. Acid treatment is especially valued to produce a stable, catalytically active form of porous crystalline magnesium silicate.

As mentioned before, certain compositions employed in the invention may be expressed according to a formula in terms of the molar ratios of oxides on a dry basis, viz.,

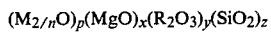

$$(M_{2/n}O)_p(MgO)_x(R_2O_3)_y(SiO_2)_z$$

wherein M is at least one ion-exchangeable cation having a valence of n; R is at least one element with valence 3+ which is not ion-exchangeable by conventional means; $x/z > 0$; $y/z \geq 0$; $p/n > y$; and p, x, z are positive numbers and y is a positive number or zero. The statement $x/z > 0$ is essential to all compositions employed in the present invention since it defines a magnesium silicate. All compositions employed in the present invention must contain magnesium.

The statement $y/z \geq 0$ indicates that this is a nonessential term. Typical nonion-exchangeable elements which may advantageously be present include by way of example, aluminum, iron, chromium, boron and gallium.

Also the above-mentioned formula could be modified to include other elements optionally present which are not ion-exchangeable by conventional means having a valence other than 3+ uch as 2+ r 4+. Germanium is an example of such an element.

Preferred embodiments of magnesium silicates employed in the present invention expressed in terms of the above formula are those wherein p is from about 0.1 to about 20; x is from about 0.1 to about 12; y is from about 0 to about 3 and z is from about 84 to about 96. It is especially preferred that the term y of the above formula be from 0 to about 1.0.

Typically, the ion-exchangeable cations M (of both the magnesium silicates represented by the above formula and similar magnesium silicates employed in the present invention) are alkali metals, hydrogen, group VIII metals or rare earth elements, or ammonium ions, but may be any element or moiety capable of exchange into the magnesium silicates of the present invention. Preferred are hydrogen, the alkali metals and the rare earth elements. Methods of ion-exchange are well-known in the art, e.g., hydrogen may be exchanged into a silicate by simply treating with acid.

Modification of the porous magnesium silicate by adding phosphorus thereto is accomplished by contacting the magnesium silicate with a phosphorus compound. Suitable phosphorus compounds may be either organic or inorganic. Representative compounds include those of the formula $PX_3$, $RPX_2$, $R_2PX$, $X_3PY$, $RP(Y)X_2$, $R_2P(Y)X$, $P_2O_5$, $R_2PO_2$, etc., wherein R is $C_{1-6}$ alkyl, phenyl, $C_{1-6}$ alkoxy or phenoxy, X is halo or hydrogen and Y is oxygen or sulfur. Additional suitable examples include salts of phosphorus acids, particularly ammonium, phosphonium, or hydrogen ammonium salts of phosphoric acid. An especially preferred phosphorus compound is ammonium hydrogen phosphate.

The phosphorus compound is employed neat or as a solution in an organic or inorganic solvent thereby simplifying contacting with the magnesium silicate and separation thereof. After contacting with the phosphorus compound the modified porous magnesium silicates of the invention are prepared by drying and calcining thereby converting the phosphorus compound to the oxide for catalytic use. Calcining may be accomplished by heating to elevated temperatures of at least about 300° C. and preferably at least about 400° C. in the presence of oxygen for a time sufficient to convert substantially all of the phosphorus to the oxide. Suitable calcination times are from about 1 hour to several hours or even days.

The phosphorus modified porous magnesium silicates of the present invention preferably contain from about 0.5 percent to about 20 percent by weight of an oxide of phosphorus calculated as phosphorus. Preferred modified compounds contain from about 1 percent to about 6 percent by weight phosphorus. A unique feature of the present compounds lies in the discovery by Applicant that in the particular alkylation of toluene by reaction with ethylene, amounts of phosphorus greater than about 6.0 percent lead to catalyst inactivation, whereas amounts of phosphorus from about 2 percent to about 5.9 percent by weight, and preferably from about 4.5 percent to 5.5 percent by weight are very effective in suppressing the formation of ortho- and meta-ethyl toluene during the reaction. The result is considered surprising since phosphorus contents in phosphorus modified aluminosilicates such as ZSM-5 are not as effective in suppressing the formation of ortho- and meta- isomers, and increasing phosphorus content in such compounds does not appear to lead to catalyst deactivation.

The above description and following examples are given to illustrate the invention and methods of making the invention, but these examples should not be taken as limiting the scope of the invention to the particular embodiments or parameters demonstrated since obvious modifications of these teachings will be apparent to those skilled in the art.

EXAMPLE 1

A solution A is made by combining 106 g of commercially available Philadelphia Quartz Sodium Silicate N ® type (trademark of Philadelphia Quartz Company) (8.90 weight percent $Na_2O$, 28.7 weight percent $SiO_2$) with 132 g of $H_2O$. A second solution B is made by combining 180 g of $H_2O$, 40 g of NaCl, 26 g of $(C_3H_7)_4NBr$, 10.2 g $MgCl_2.6H_2O$ and 8 g of concentrated $H_2SO_4$ (96 weight percent) to form a clear solution.

Solution A is transferred to a Waring ® blender and the blender is started at the "high" setting. Solution B is added at once and the mixture is stirred vigorously for 1 minute. The resulting slurry is then placed inside a stainless steel autoclave, heated to about 150° C. under autogenous pressure and stirred. After 24 hours, the autoclave is cooled to room temperature and the solid product is isolated by filtration. The filter cake is washed several times with much water and then air dried at about 110° C. into a free flowing powder.

The above prepared porous magnesium silicate is calcined for 15 hours at 550° C. in air to remove the quaternary ammonium salt from the internal pores. Next, the material is slurried with 1.0N $NH_4NO_3$ solution, at a temperature of at least 80° C. overnight. The resulting material is filtered, washed with D.I. water and dried at 110° C.

Ten grams of this material is spread into a thin layer in a large petri dish and sufficient $(NH_4)HPO_4$ solution (25 weight percent concentration) is added dropwise to the powder with a syringe to provide 4.7 percent phosphorous based on dry catalyst weight. The moistened powder is then mixed well with a spatula. The powder is first dried at room temperature and then at 110° C. The dried catalyst is mixed with kaolin clay, ½ part clay per part catalyst, and enough water is added to form a moist cake. The cake is dried, first at room temperature, then at 110° C., and then calcined at 550° C. for 5 hours in air.

The calcined catalyst is crushed and tested in the alkylation of toluene with ethylene. Eight grams of catalyst are loaded in a ½-inch diameter stainless steel reactor tube. The operating conditions of the reaction are: temperature 410° C., pressure 100 psi, toluene flow rate 104.7 g/hr, ethylene flow rate 60 cc/min, $H_2$ flow rate 140 cc/min, WHSV=13, molar ratio toluene/ethylene=7.6, molar ratio ethylene/hydrogen=2.3. Data are obtained during a continuous run lasting four days. At the end of two days, the temperature is increased to 440° C. The initial ethylene conversion is about 80 percent falling to a level of about 60 percent prior to increase in reaction temperature. Selectivity to para ethyltoluene is at least 96 percent during the entire reaction period.

What is claimed is:

1. A process for alkylating aromatic hyrocarbons comprising contacting an alkylating agent with an aromatic hydrocarbon to form a reaction mixture under alkylation conditions in the presence of a catalytically effective amount of a porous crystalline magnesium silicate modified by addition thereto of phosphorus in the amount of from about 0.25 percent to about 30 percent by weight.

2. A process according to claim 1 wherein the phosphorus modified porous crystalline magnesium silicate is modified by addition thereto of phosphorus in an amount from about 1 percent to about 6 percent by weight.

3. A process according to claim 2 wherein the alkylating agent is ethylene and the aromatic hydrocaron is toluene.

4. A process according to claim 1 wherein the phosphorus modified crystalline magnesium silicate corresponds to the following formula in terms of molar ratios of oxide on a dry basis $$(M_{2/n}O)_p(MgO)_x(R_2O_3)_4(SiO_2)_z$$

wherein M is at least one cation having a valence n; R is a trivalent element or mixture thereof; x/z>0; y/z≧0; p/n>y; and p, x, z are positive numbers and y is a positive number or zero.

* * * * *